United States Patent [19]

Kawatra et al.

[11] Patent Number: 4,916,719
[45] Date of Patent: Apr. 10, 1990

[54] ON-LINE ANALYSIS OF ASH CONTAINING SLURRIES

[75] Inventors: Surendra K. Kawatra; Lawrence L. Sutter; Timothy C. Eisele, all of Houghton, Mich.

[73] Assignee: Board of Control of Michigan Technological University, Houghton, Mich.

[21] Appl. No.: 203,323

[22] Filed: Jun. 7, 1988

[51] Int. Cl.$^4$ .......................................... G01N 23/223
[52] U.S. Cl. ...................................... 378/46; 378/47; 378/88; 138/37
[58] Field of Search .................................. 378/44–47, 378/50, 51, 53, 54, 86, 88–90; 138/37, 39, 42, 43; 73/863.41, 863.43

[56] References Cited

U.S. PATENT DOCUMENTS

| | | | |
|---|---|---|---|
| 2,878,831 | 3/1959 | Farnham et al. | 138/43 |
| 3,270,204 | 8/1966 | Rhodes | 250/83.3 |
| 3,889,113 | 6/1975 | Rhodes | 378/45 |
| 4,090,074 | 5/1978 | Watt et al. | 378/53 |
| 4,282,434 | 8/1981 | Lyman | 378/89 |
| 4,388,530 | 6/1983 | Lubecki | 378/45 |
| 4,450,576 | 5/1984 | Lubecki | 378/47 |
| 4,486,894 | 12/1984 | Page | 378/46 |
| 4,566,114 | 1/1986 | Watt | 378/88 |

FOREIGN PATENT DOCUMENTS

| | | | |
|---|---|---|---|
| 0965303 | 7/1964 | United Kingdom | 378/88 |
| 2083618 | 3/1982 | United Kingdom | 378/45 |

OTHER PUBLICATIONS

"The On-Line Measurements of Ash in Coal Slurries" by Itawatra et al.

Primary Examiner—Craig E. Church
Assistant Examiner—John C. Freeman
Attorney, Agent, or Firm—Michael, Best & Friedrich

[57] ABSTRACT

The ash content of coal suspended in a slurry is determined by bombarding a sample of the slurry flowing past a window of a measuring chamber with radiation from an annular nucleonic source, such as Cm-244, for emitting radiation within the range of about 7 to about 30 KeV and causing the sample to emit both backscattered and iron fluorescent x-rays. These x-rays are detected by a radiation detector which produces first and second electrical signals representative of the intensity of each. The density of the sample flowing from the measuring chamber is measured, such as by a nucelonic density gauge, to produce an electrical signal representative of the density and the ash content is determined from the detected intensities of the backscattered and iron fluorescent x-rays and the sample density.

5 Claims, 2 Drawing Sheets

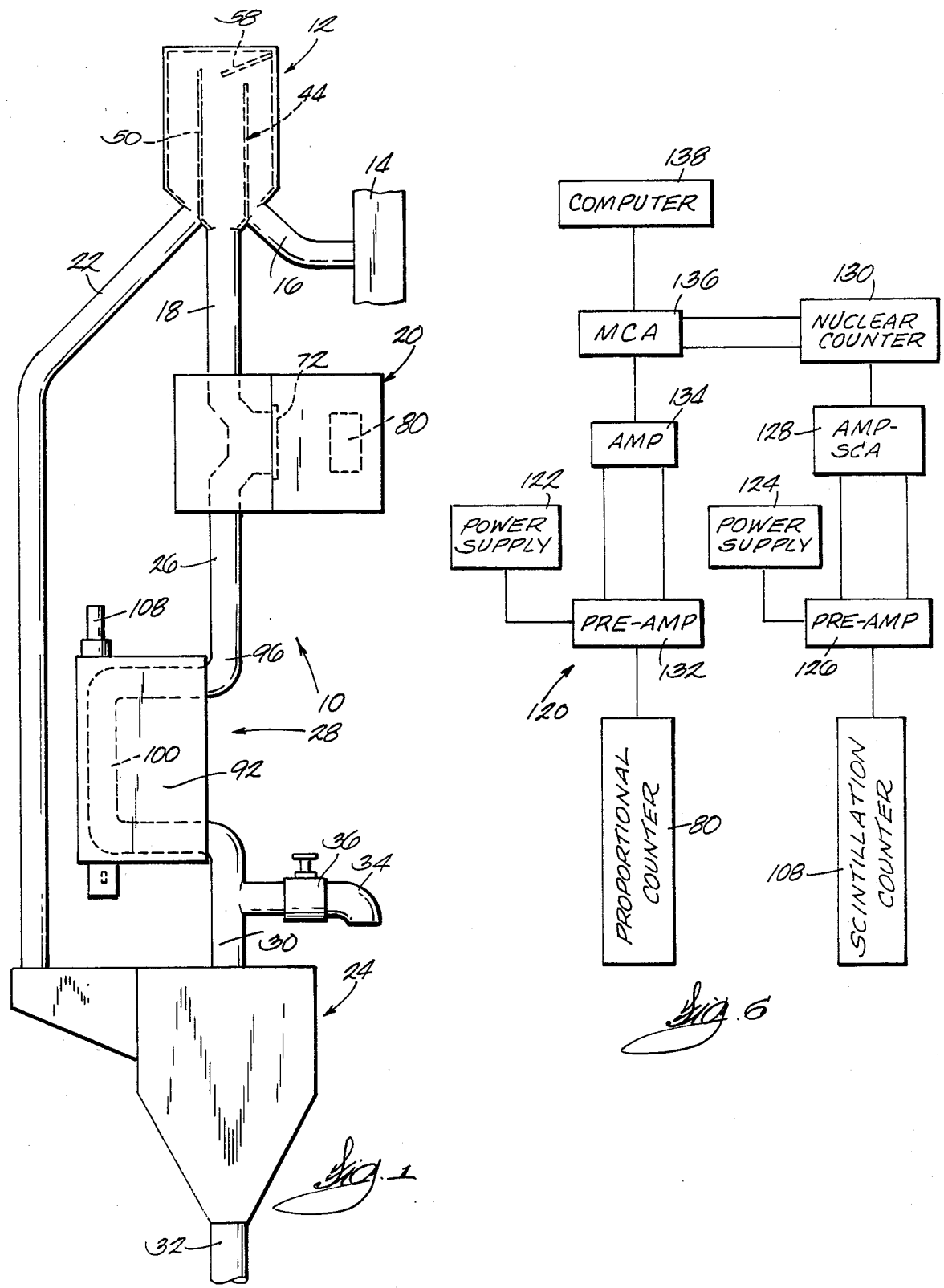

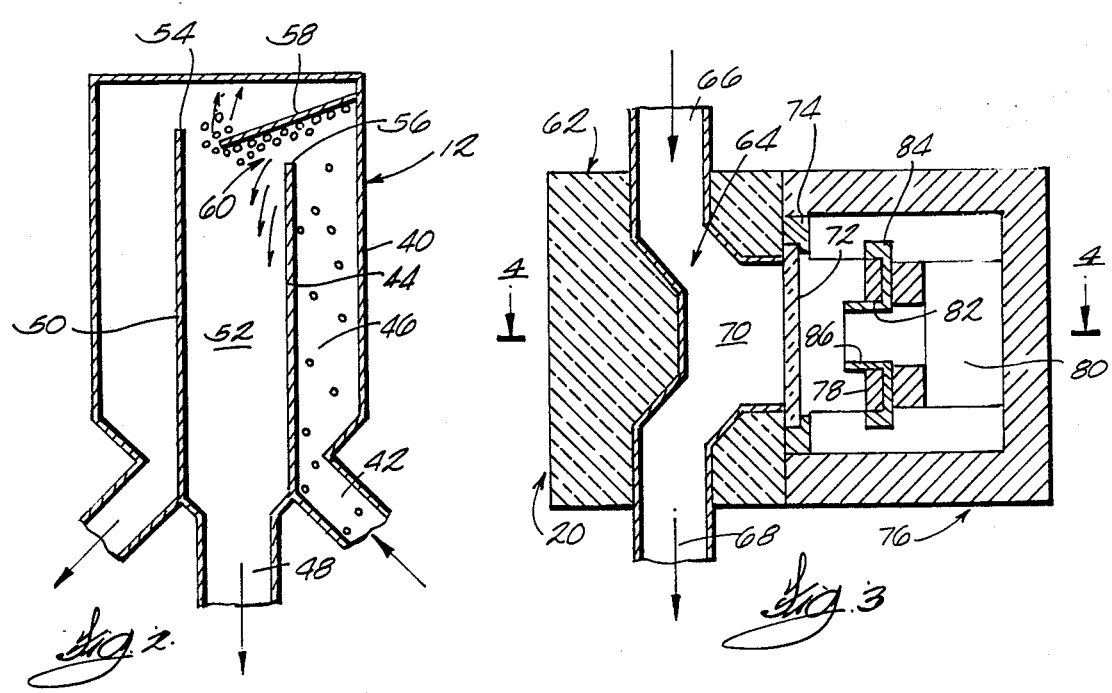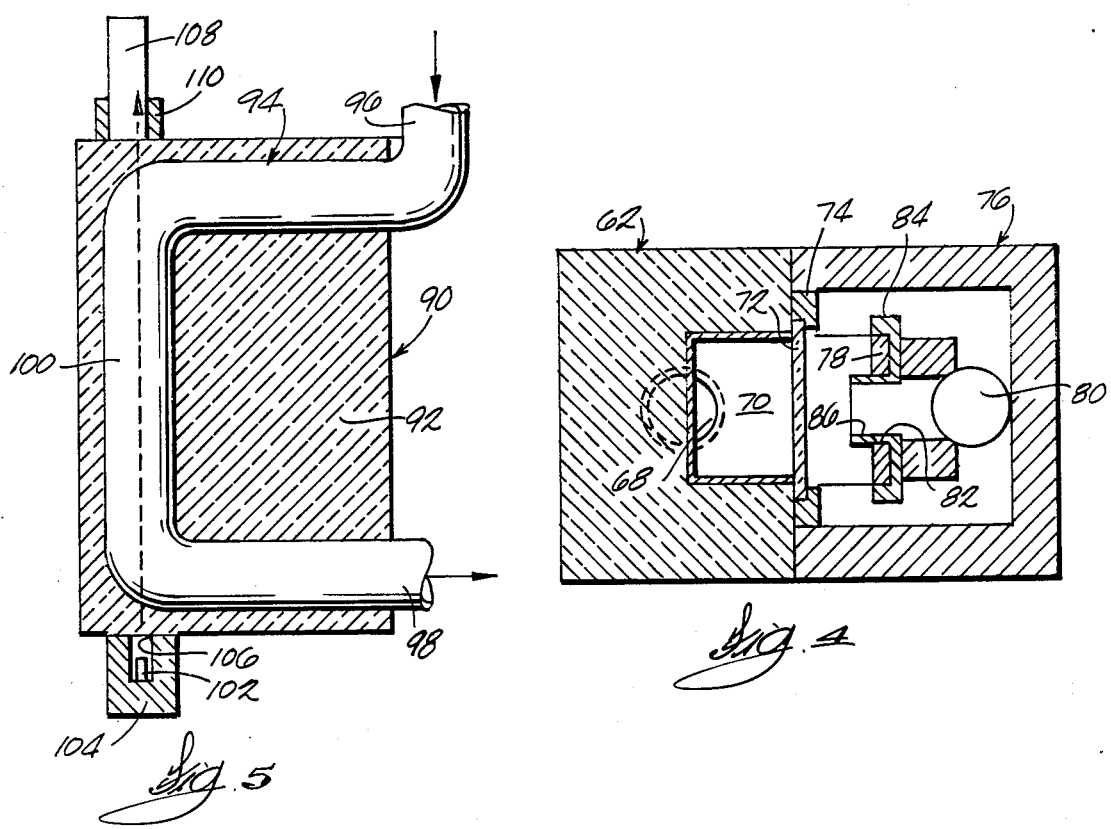

ON-LINE ANALYSIS OF ASH CONTAINING SLURRIES

BACKGROUND OF THE INVENTION

This invention relates to methods and apparatus for determining the ash content in ash-containing slurries. In one aspect, the invention relates to methods and apparatus for making an on-line measurement of the ash content of coal in an aqueous slurry.

Because of the low price of coal in the past, only very simple and inexpensive processing methods were employed to reduce the content of ash-forming inorganic materials prior to burning. The price of coal is now several times what it was ten years ago and more sophisticated coal-cleaning processes now are cost justified. The productivity and/or product quality of such cleaning processes depends to a large extent on process control. An important part of an effective process control is the capability of continuously monitoring the ash content of a coal so that process conditions can be changed in response to changes in the composition of the coal entering a plant. Such a capability is also useful in process control for other applications, such as coal liquification and gasification and coal-water fuel production.

The most widely used methods and devices for measuring the ash content of coal employ either x-ray fluorescence analysis or a comparison of Compton and Rayleigh intensities. Representative prior art devices are disclosed in the following patents:

| Patents | U.S. Pat. No. | Issue Date |
| --- | --- | --- |
| Rhodes | 3,270,204 | August 20, 1966 |
| Lubecki et al. | 4,388,530 | June 14, 1983 |
| Lubecki et al. | 4,450,576 | May 22, 1984 |
| Page et al. | 4,486,894 | December 4, 1984 |
| Watt et al. | 4,566,114 | January 21, 1986 |

Such prior devices typically are quite expensive and/or imprecise.

SUMMARY OF THE INVENTION

An object of the invention is to provide an improved, relatively inexpensive device and method for making rapid measurements of the ash content of coal in a slurry.

Another object of the invention is to provide such a device and method which can be used to make a continuous, on-line analysis of a process stream.

A further object of the invention is to provide such a device and method which is capable of making accurate measurements in spite of significant changes in the composition and conditions of the slurry.

Other objects, aspects and advantages of the invention will become apparent to those skilled in the art upon reviewing the following detailed description, the drawings and the appended claims.

The method for determining the suspended ash content of coal suspended in a slurry provided by the invention includes the steps of bombarding a sample of the slurry with radiation from a nucleonic source which emits radiation within a range of about 7 to about 30 KeV to cause the sample to emit both backscattered and iron fluorescent x-rays, detecting the intensity of the backscattered and iron fluorescent x-rays, measuring the density of the sample and determining from the detected intensities of the backscattered and iron fluorescent x-rays and the sample density the ash content of the coal.

In one embodiment, the density of the sample is determined by directing a gamma-ray beam through the sample, detecting the intensity of the gamma-rays transmitted through the sample and determining the density of the sample as a function of the detected gamma-ray intensity. The ash content of the coal is determined in accordance with the equation:

$$A = K_1(BS) + K_2(FeK\alpha) + K_3(T) + C \quad (1)$$

where
 $A$ = weight % ash in coal
 $BS$ = backscattered x-ray intensity
 $FeK_\alpha$ = iron $K_\alpha$ fluorescence intensity
 $I$ = gamma-ray transmission intensity
 $K_1, K_2, K_3, C$ = constants The device provided by the invention includes a measuring chamber having a window at one side, a nucleonic source for emitting radiation within the above-noted range through the window and into the sample, a radiation detector for detecting backscattered and iron fluorescent X-rays emitted from the sample and producing first and second electrical signals representative of the intensity of each, means for determining the density of the sample and producing a third electrical signal representative of the sample density, and means for receiving the first, second and third electrical signals and producing a fourth electrical signal representative of the ash content of the coal in the sample.

The source preferably is Cm-244 and preferably has an annular shape with a central opening through which the backscattered and iron fluorescent x-rays emitted form the sample are transmitted to the radiation detector.

In one embodiment, the density-measuring means includes a flow passage, a nucleonic source for transmitting a gamma-ray beam through the sample passing through the flow passage, and a radiation detector for detecting the gamma rays transmitted through the sample and producing a signal representative of the intensity of the coal slurry.

In one embodiment, the device includes a pressure control unit upstream of the measuring chamber for removing air bubbles from an on-line sample stream and maintaining the sample introduced into the measuring chamber at a constant pressure. The pressure control unit includes a tank having a baffle arrangement which allows a relatively high throughput with minimum splashing and level fluctuations.

BRIEF DESCRIPTION OF THE DRAWINGS

FIG. 1 is a schematic representation of a device embodying the invention.

FIG. 2 is an enlarged schematic view of the pressure control unit of the device illustrated in FIG. 1.

FIG. 3 is an enlarged sectional view of the ash sensing unit of the device illustrated in FIG. 1.

FIG. 4 is a sectional view taken generally along line 4—4 in FIG. 3.

FIG. 5 is an enlarged sectional view of the density gauge of the device illustrated in FIG. 1.

FIG. 6 is a block diagram of the electrical circuit for the device illustrated in Fig. 1.

DETAILED DESCRIPTION

The device and method provided by the invention for measuring the ash content of coal in a slurry is based primarily on the intensity of x-rays backscattered from a coal slurry. When a material is irradiated with x-rays, a certain portion of the x-ray photons are backscattered therefrom and the backscattered radiation is a function of the Compton and Rayleigh scattering probabilities and the depth of penetration of the x-rays into the material. When these effects are considered together, the following results may be noted.

Compton scatter has a tendency to decrease with an increasing elemental atomic number. Therefore, increasing the atomic number of the scattering material will rapidly decrease the Compton scattered intensity. Although the Rayleigh scattering probability increases as the square of the atomic number, this is not sufficient to compensate for the decrease in penetration depth which is proportional to the atomic number cubed. Therefore, the Rayleigh scatter decreases gradually with increasing atomic number and the net effect is that the overall intensity of backscattered radiation decreases as the atomic number of the scattering material increases.

The theoretical basis of this invention is that measurements of the scattering of low-energy x-rays from a material can be applied to chemical analysis or the ash content of coal in a slurry in this case. That is, if the amount of high atomic number material (ash) varies in a low atomic number matrix (coal), the effective atomic number, and hence the intensity of scattered radiation, will vary accordingly.

Coal ash is the oxidized residue remaining after coal has been burned and consists essentially of alumina, silica, iron minerals and compounds and small quantities of the oxides of potassium, calcium, titanium, etc. In coal, the effective atomic number of ash is about 10, while that of the combustible carbonaceous material is about 6. Since the effective atomic number of coal increases with increasing ash content, the ash content can be theoretically determined by measuring the intensity of scattered low-energy photons.

The content of iron-sulfur minerals in coal, such as pyrite and pyrrhotite, may be as high as 5 to 10 weight %. These minerals have an effective atomic number of about 20 and their presence will cause greater changes in scattering intensity than alumina and silica which have an effective atomic number of about 10. Accordingly, compensation should be made for the iron content in order to accurately determine the ash content. If a coal slurry is bombarded by radiation from a nucleonic source which excites $FeK_\alpha$(6.4 KeV) radiation and the intensity of the iron fluorescent x-rays and backscattered x-rays are measured concurrently, quantitative measurement of the iron-sulfur mineral content in the slurry can be made and this measurement provides a correction for the additional scattering due to the iron-sulfur minerals.

Backscatter measurements alone are not sufficient to obtain an accurate measure of the ash content of coal in a slurry. Backscatter measurements do not distinguish between atomic number changes due to changing ash content and fluctuations due to changing content of carrier liquid, e.g., water. A correction for the slurry water content can be most readily obtained by measuring the slurry density. While the slurry density can be determined by various suitable means, including a variety of mechanical means, in a preferred embodiment it is measured by a radiation adsorption technique by which the intensity of a gamma-ray beam transmitted through the slurry is measured.

When density is measured by this gamma-ray technique, the ash content of coal in the slurry is determined in accordance with equation (1) above.

FIG. 1 illustrates a device 10 for determining the ash content of coal suspended in a slurry in accordance with the invention. In the specific embodiment illustrated, the device 10 is capable of making a continuous on-line analysis of a process stream.

The device 10 includes a pressure control unit 12 into which a flow of a sample of a coal slurry from a process stream 14 can be continuously introduced via a slurry sample conduit 16. The sample is maintained at a substantially constant head pressure in the pressure control unit 12 as described in more detail below and a portion flows therefrom and through a sample supply conduit 18 into a sensing unit 20. Another portion of the sample flowing into the pressure control unit 12 overflows therefrom through an overflow conduit 22 and is collected in a sump 24. As a sample flows from the sensing unit 20, it is bombarded with radiation and the backscattered and iron fluorescent x-rays are detected as described in more detail below. The sample flows from the sensing unit 20 through a conduit 26 into a density-measuring means 28 and flows therefrom through a conduit 30 into the sump 24.

The slurry collected in the sump 24 from the pressure control unit 12 and the density-measuring means 28 can be returned to the process stream 14 or discharged to waste via a conduit 32. Samples of the slurry exiting from the density-measuring means 28 can be collected for calibration purposes through a sampling port 34 including a control valve 36.

Referring to FIG. 2, the pressure control unit 12 includes a tank 40 which preferably is located above the sensing unit 20 and is designed to remove air bubbles from the incoming slurry sample and to maintain the sample supplied to the sensing unit 20 at a constant head pressure. This is accomplished through an arrangement of baffles which allow a relatively high throughput of slurry with minimum splashing and liquid level fluctuations.

More specifically, the tank 40 includes a slurry inlet 42 in the lower portion, through which the incoming slurry sample flows, an upwardly extending inlet baffle 44 which defines an inlet chamber 46 in communication with the slurry inlet 42, a sample outlet 48, an upwardly extending overflow baffle 50 spaced transversely from the inlet baffle 44 and cooperating therewith to define a sample supply chamber 52 in communication with the sample outlet 48. The upper edge 54 of the overflow baffle 50 is located above the upper edge 56 of the inlet baffle 44. Extending from one side of the tank 40 and spaced above the upper edge of 56 of the inlet baffle 44 is an anti-splash plate 58.

Slurry entering the tank 40 through the slurry inlet 42 travels upwardly, impinges the anti-splash plate 58, passes through the opening 60 between the anti-splash plate 58 and the upper edge 56 of the inlet baffle into the sample supply chamber 52 and flows from the sample supply chamber 52 through the outlet 48 enroute to the sensing unit 20. Thus, the slurry enters the sample supply chamber 52 under relatively quiescent conditions. The resulting relatively high throughput of the sample minimizes particles settling in the tank 40, thereby ensuring that the composition of the stream being measured is representative of the entire sample.

Excess slurry flows over the overflow baffle 50 and exits from the tank 40 through the overflow conduit 22. Thus, the overflow baffle 50 maintains a constant slurry level, and hence a constant head pressure, in the sample supply chamber 52.

Air bubbles in the sample can affect the measurements made by the density-measuring means 28. The anti-splash plate 58 preferably is located at an incline as illustrated to permit the removal of air bubbles in the incoming slurry sample. A substantial portion of the air bubbles coalesce when the slurry impinges the anti-splash plate 58, rise to the surface of the sample supply chamber 52 and subsequently escape to the atmosphere. For this purpose, the tank 40 can be open or have a substantially unobstructed vent port.

Referring to FIGS. 3 and 4, the sensing unit 20 has a housing 62 including a measuring chamber 64 through which the sample flows. The measuring chamber 64 has an inlet 66 connected in communication with the conduit 18, an outlet 68 connected in communication with the conduit 26 and a flow passage 70 extending between the inlet 66 and outlet 68. Located midway between the inlet 66 and the outlet 68 and at one side of the flow passage 70 is a measuring window 72 through which radiation for bombarding the sample and the backscattered radiation are transmitted. While the housing 62 can be made from various suitable materials, it preferably is made from a transparent material, such as Plexiglas. The measuring window 72 is made from a material through which x-rays are readily transmitted with minimum interference, preferably a wear-resistant, transparent material such as Mylar. The measuring window 72 preferably is removably mounted on the housing 62, such as by a removable mounted holding fixture 74, so it can be replaced in the vent of wear during use.

The sensing unit 20 also has a radiation section 76 including a nucleonic radiation source 78 for emitting x-rays through the measuring window 72 into the sample flowing through the flow passage 70 and a sensor or detector 80 for detecting backscattered and iron fluorescent x-rays emitted by the sample and producing electrical signals representative of the intensity of each.

In order to obtain maximum sensitivity to changes in the effective atomic number, the source 78 should be capable of producing x-ray energies within the range of about 7 to about 30 KeV. Nucleonic sources or radioisotopes with this capability include Am-241, Cd-109, Fe-55, Co-57, Te-123m, Y-88, Pb-210, I-125, Pu-238 and Cm-244. Cm-244 and Pu-238 are preferred because of their low selfabsorption, long half-lives and ability to excite iron-fluorescent x-rays without overlapping the fluorescent peak. Cm-244 is the most preferred source because of its high saturation loading.

While a point source for emitting a collimated x-ray beam can be used for slurries having higher ash contents, it usually does not provide adequate sensitivity for coals containing 1% or less ash. The nucleonic radiation source 78 preferably has an annular shape with a central opening 82 through which the backscattered and iron-fluorescent x-rays from the slurry sample are transmitted to the detector 80. The source 78 can have an outside diameter approximating the opening of the measuring window 72 and preferably is situated to be parallel with and centered on the measuring window 72. Such an arrangement exposes a larger quantity of the slurry sample to radiation and provides a more uniform irradiation, while permitting transmission of backscattered and iron-fluorescent x-rays to the detector 80.

The radiation source 78 is mounted in a collimator 84 which covers at least the back surface and inner wall of the radiation source to prevent x-rays from being emitted directly toward the detector 80. The collimator 84 preferably is made from lead because a smaller thickness can be used to effectively shield x-rays from the source 78, thereby permitting a larger opening 86 for transmission of backscattered and iron-fluorescent x-rays to the detector 80. The detector 80 is enclosed in an aluminum housing 88.

Various conventional detectors capable of discriminating the spectra of the backscattered and iron-fluorescent x-rays can be used to detect the backscattered and iron-fluorescent x-rays transmitted through the collimator opening 86, such as a scintillation counter or a xenon-filled proportional counter which is preferred because it has a higher energy resolution.

A sensing device utilizing backscattered radiation is more sensitive to material near the measuring window. For this reason, the flow passage 70 preferably is arranged with an off set path so that the sample is forced to impinge directly on the measuring window 72 and also is contoured to prevent particles from collecting in any area.

While a wide variety of suitable density-measuring means and techniques can be used to determine the density of the slurry sample, in the specific embodiment illustrated, such means is a density gauge 90 employing gamma-ray radiation. Referring to FIG. 5, the density gauge 90 includes a housing 92, preferably made from a transparent material such as Plexiglas, and a generally C-shaped flow passage 94 extending between an inlet 96 connected to the conduit 26 and an outlet 98 connected in communication with the conduit 30. The flow passage 94 has a generally vertical section 100.

Located near the lower end of the vertical section 100 is a nucleonic radiation source 102 for transmitting a gamma-ray beam longitudinally through the vertical section, and thus through the slurry sample flowing downwardly through the vertical section 100. The gamma-ray source 102 preferably is a point source and can be a suitable radioisotope useful for measuring the solids contents of coal slurries. Suitable nucleonic sources of radioisotopes include Ce-139, Ir-192, Co-57 and Gd-153 with Gd-153 being preferred because of its higher sensitivity and acceptable half-life. The gamma-ray source 102 is situated in a lead housing 104 including a cylindrical recess 106 so that the housing also serves as a collimator.

Located near the upper end of the vertical section 100 is a detector 108 for detecting the gamma-rays transmitted through the slurry and producing an electrical signal representative of the intensity thereof. Various conventional detectors can be used for this purpose, such as a scintillation counter using a thallium-activated sodium iodide crystal which has a high detection efficiency for gamma-rays. The sensor portion of the detector 108 can be shielded with a lead sleeve 110 as illustrated.

The length of the vertical section 100 can be varied to provide the highest sensitivity to density change and generally is on the order of about 20 centimeters for many slurries. Downward flow through the flow passage 94 is preferred in order to minimize settling of small particles during passage therethrough and a resulting erroneous high density reading.

The detectors 80 and 108 are connected in a suitable electrical system for producing a visual readout and/or printout of the ash content. FIG. 6 is a block diagram of an exemplary electrical system.

Referring to FIG. 6, the electrical system 120 includes a high voltage supply 122 which supplies the voltage for operating the backscattered x-ray detector (proportional counter) 80 and another high voltage supply 124 which supplies the voltage for operating the gamma-ray detector (scintillation counter) 108. A preamplifier 126 distributes high voltage to the dynodes of the photomultiplier of the scintillation counter 108 and amplifies the counter signal for transmission to an amplifier/single channel analyzer (AMP/SCA) 128 which produces a digital pulse for every x-ray pulse detected by the scintillation counter 108 within a predetermined energy range. This permits the use of a single gamma-ray energy in determining the amount of radiation absorbed by the slurry. A nuclear counter 130 counts the number of pulses generated by the AMP/SCA 128 which is proportional to the density of the slurry.

The signals from the proportional counter 80 are first amplified by a preamplifier 132 and then by an amplifier 134 which amplifies them to improve the signal-noise ratio before transmission to a multichannel analyzer (MCA) 136 which converts the pulses to digital information. The MCA 136 stores and displays the spectra of the backscattered and iron-fluorescent x-rays. It measures the energy of incoming x-ray pulses and graphically displays the number of pulses at different energy levels. Once a spectrum has been accumulated, the integral of a predetermined area of the spectrum is calculated by the MCA 136. Signals representative of the intensities of the backscattered and iron-fluorescent x-rays from the MCA 136 and of the slurry density from the nuclear counter 130 are transmitted to a computer or microprocessor 138, e.g., a HP-85 microprocessor marketed by Hewlett-Packard, which is programmed to calculate the ash content in accordance with equation (1) above. The microprocessor 138 can provide output signals for operating a printer, digital readout device, means for controlling process variables, etc.

Tests have been run on a laboratory model of a device like that illustrated in the drawings, using an annular Cm-244 source in the sensing unit 20 and a 100 millicuri Gd-153 point source in the density gauge 90, on a variety of aqueous coal slurries. This device was shown to be capable of measuring the ash content of coal and slurries to within ±0.32% ash at 15 weight % solids.

From the foregoing description, one skilled in the art can easily ascertain the essential characteristics of the invention and, without departing from the spirit and scope thereof, make various changes and modifications to adapt it to various usages.

We claim:

1. A device for measuring the ash content of coal suspended in a slurry comprising
   a pressure control unit for receiving a continuous flow of the coal slurry to be measured, said pressure control unit comprises
      a tank located above said measuring chamber and having a slurry inlet, a sample outlet and an overflow outlet,
      an upwardly extending inlet baffle in said tank having an upper edge and defining an inlet chamber communicating with said slurry inlet, and
      an upwardly extending overflow baffle in said tank having an upper edge and spaced from said baffle to define a sample chamber communicating with said sample outlet, said overflow bubble having an upper edge located above the upper edge of said inlet baffle so as to maintain the coal slurry sample in said sample chamber at a substantially constant level; a backscatter sensing unit comprising
   a measuring chamber having a first inlet in communication with said sample outlet of said pressure control unit, a first outlet, a flow passage extending between said first inlet and said first outlet and a measuring chamber at side of said flow passage between said first inlet and said outlet, said flow passage being arranged so that a coal slurry sample passing therethrough impinges directly upon said measuring window,
   an annular nucleonic source having a central opening for emitting radiation within the range of about 7 to about 30 KeV through said measuring window and uniformly radiating the sample impinging on said measuring window, and
   a radiation detector for measuring backscattered and iron fluorescent X-rays emitted from the irradiated sample and passing through the central opening of said source and for producing second electrical signals representative of the intensity of the backscattered X-rays and the iron fluorescent X-rays, respectively;
   means for measuring the density of the sample and producing a third electrical signal representative of the sample density; and
   computer means for receiving said first, second and third electrical signals, for using said first electrical signal as an approximation of the ash content of the slurry, said second electrical signal as a correction for high atomic number elements in the coal and said third electrical signal as a correction for the quantity of water in the slurry and for producing a fourth electrical signal representative of the ash content of the coal in the sample.

2. A device according to claim 1 wherein said annular source is Cm-244.

3. A device according to claim 1 wherein said density-measuring means includes
   a flow passage including a second inlet and a second outlet;
   a nucleonic source for transmitting a gamma-ray beam through the sample passing through said flow passage; and
   a radiation detector for detecting the gamma-rays transmitted through the sample and producing said third signal.

4. A device according to claim 3 wherein
   said flow passage extending between said second inlet and said second outlet is generally C-shaped and includes a generally vertical section through which the sample flows downwardly from said second inlet toward said second outlet;
   said gamma-ray source is situated to transmit a gamma-ray beam longitudinally through said vertical section; and
   said detector includes a sensor portion situated to receive gamma-ray transmitted through the sample flowing through said vertical section.

5. A device according to claim 1 wherein said pressure control unit further includes
   an anti-splash plate which is located in said tank above said upper edge of said inlet baffle and is impinged by the coal slurry flowing from said inlet chamber toward said sample chamber, said anti-splash plate being arranged to cause air bubbles in the coal slurry to coalesce and to be directed upwardly toward the top of said tank.

* * * * *

UNITED STATES PATENT AND TRADEMARK OFFICE
CERTIFICATE OF CORRECTION

PATENT NO. : 4,916,719

DATED : April 10, 1990

INVENTOR(S) : Surendra K. Kawatra, et al.

It is certified that error appears in the above-identified patent and that said Letters Patent is hereby corrected as shown below:

Column 2, line 10, the equation should read:
$$A=K_1(BS)+K_2(FeK\alpha)+K_3(I)+C$$

Claim 1, Column 7, line 67, "bubble" should be --baffle--.

Claim 1, Column 8, line 22, after "producing", insert --first and--.

Signed and Sealed this

Eleventh Day of June, 1991

Attest:

HARRY F. MANBECK, JR.

Attesting Officer     Commissioner of Patents and Trademarks